(12) United States Patent
Kuslys

(10) Patent No.: US 10,624,377 B2
(45) Date of Patent: Apr. 21, 2020

(54) EDIBLE WEB COMPRISING MICROORGANISMS

(71) Applicant: NESTEC S.A., Vevey (CH)

(72) Inventor: Martinas Kuslys, Grosshoechstetten (CH)

(73) Assignee: Societe des Produits Nestle S.A., Vevey (CH)

( * ) Notice: Subject to any disclaimer, the term of this patent is extended or adjusted under 35 U.S.C. 154(b) by 268 days.

(21) Appl. No.: 14/349,556

(22) PCT Filed: Oct. 5, 2012

(86) PCT No.: PCT/EP2012/069682
§ 371 (c)(1),
(2) Date: Apr. 3, 2014

(87) PCT Pub. No.: WO2013/050511
PCT Pub. Date: Apr. 11, 2013

(65) Prior Publication Data
US 2014/0248246 A1  Sep. 4, 2014

(30) Foreign Application Priority Data
Oct. 6, 2011 (EP) ..................................... 11184134

(51) Int. Cl.
| | | |
|---|---|---|
| A23L 33/10 | (2016.01) | |
| A23L 33/135 | (2016.01) | |
| A23P 20/20 | (2016.01) | |
| A61K 35/741 | (2015.01) | |
| A61K 35/742 | (2015.01) | |
| A61K 35/744 | (2015.01) | |
| A61K 35/745 | (2015.01) | |
| A61K 35/747 | (2015.01) | |
| A61K 35/76 | (2015.01) | |
| A61K 9/00 | (2006.01) | |
| A23P 20/25 | (2016.01) | |
| A61K 9/70 | (2006.01) | |

(52) U.S. Cl.
CPC ............. *A23L 33/10* (2016.08); *A23L 33/135* (2016.08); *A23P 20/20* (2016.08); *A61K 9/0056* (2013.01); *A61K 35/742* (2013.01); *A61K 35/744* (2013.01); *A61K 35/745* (2013.01); *A61K 35/747* (2013.01); *A61K 35/76* (2013.01); *A23P 2020/253* (2016.08); *A61K 9/0053* (2013.01); *A61K 9/7007* (2013.01)

(58) Field of Classification Search
None
See application file for complete search history.

(56) References Cited

U.S. PATENT DOCUMENTS

| | | | | |
|---|---|---|---|---|
| 2004/0109932 A1* | 6/2004 | Chen | ........................ | A23G 3/36 426/660 |
| 2005/0079253 A1* | 4/2005 | Nakamura | ........... | A61K 9/0056 426/138 |
| 2007/0231435 A1* | 10/2007 | Ream | .................... | A23G 3/0021 426/383 |
| 2009/0208577 A1* | 8/2009 | Xu | ........................... | A61L 27/38 424/484 |
| 2009/0214709 A1* | 8/2009 | Fuhrmeister | ........... | A23G 3/343 426/61 |
| 2010/0089860 A1* | 4/2010 | Wiggins | ............... | B65D 51/225 215/47 |
| 2010/0247712 A1* | 9/2010 | Rudolph | .............. | A23C 9/1232 426/61 |
| 2016/0066596 A1 | 3/2016 | Elejalde et al. | | |

FOREIGN PATENT DOCUMENTS

| | | |
|---|---|---|
| CN | 101453904 | 6/2009 |
| CN | 101773221 | 7/2010 |
| CZ | 300697 | 7/2009 |
| EP | 1417895 | 5/2004 |
| JP | 6030647 | 2/1985 |
| JP | 03076561 | 4/1991 |
| JP | 07135917 | 5/1995 |
| JP | 07184531 | 7/1995 |
| JP | 10146157 | 6/1998 |
| JP | 2000093127 | 4/2000 |
| JP | 2007507209 | 3/2007 |
| JP | 2010132653 | 6/2010 |
| WO | 2011117012 | 9/2011 |
| WO | WO-2012048914 A1 * | 4/2012 ............ A61J 7/0038 |

OTHER PUBLICATIONS

Japanese Office Action for Application No. P2014-533912, Dispatch No. 188358, Dispatch Date Apr. 26, 2016, 6 pages.

* cited by examiner

*Primary Examiner* — Sharmila G Landau
*Assistant Examiner* — Paul D Pyla
(74) *Attorney, Agent, or Firm* — K&L Gates LLP

(57) ABSTRACT

The present invention relates to edible webs comprising microorganisms, such as probiotics. In particular, the present invention relates to an edible web having microorganisms, such as bacteria, probiotic bacteria, bacteriophages or viruses printed thereon, e.g. by the use of inkjet printing. In addition the invention relates to methods of producing such edible webs, to various products comprising the edible webs as well as to use of the edible webs comprising microorganisms.

8 Claims, No Drawings

EDIBLE WEB COMPRISING MICROORGANISMS

CROSS REFERENCE TO RELATED APPLICATIONS

The present application is a National Stage of International Application No. PCT/EP2012/069682, filed on Oct. 5, 2012, which claims priority to European Patent Application No. 11184134.2, filed Oct. 6, 2011, the entire contents of which are being incorporated herein by reference.

TECHNICAL FIELD OF THE INVENTION

The present invention relates to edible webs comprising microorganisms, such as bacteria, probiotic bacteria, bacteriophages or viruses. In particular, the present invention relates to an edible web having microorganisms, such as bacteria, probiotic bacteria, bacteriophages or viruses printed thereon, e.g. by the use of inkjet printing.

BACKGROUND OF THE INVENTION

It is generally accepted that certain types of microorganisms may positively affect the health of a human or an animal, when administered through oral intake. Examples of such microorganisms are probiotics. According to the currently adopted definition by FAO/WHO, probiotics are: "Live microorganisms which when administered in adequate amounts confer a health benefit on the host". Lactic acid bacteria and bifidobacteria are the most common types of microbes used as probiotics; but certain yeasts and bacilli may also be helpful. Probiotics are commonly consumed as part of fermented foods with specially added active live cultures; such as in yogurt, soy yogurt, or as dietary supplements.

However, since probiotics confer their effect by being viable during intake, it may be an obstacle to obtain high enough concentrations of viable probiotics (cell forming units; CFU), which are stable over a longer period of time, for example when stored before consumption.

When stored in a liquid state, such as in yoghurt, probiotics may not be viable for long periods of time. In addition, when stored in a liquid state it may be necessary to keep the products cooled which may be problematic and costly and due to the presence of liquid in the product it requires more room for storage. When stored in a dry state it may be difficult to control the exact concentration (CFU) of the probiotics.

Thus, several problems with the current technology relating to probiotics exist, which may be overcome with the present invention.

Merrin et al. discloses printing of different strain of genetically modified *E. coli* bacteria on flat surfaces such as glass plates, agar plates and nitrocellulose sheets using inkjet printers (Merrin et al. Printing Multistrain Bacterial Patterns with a Piezoelectric Inkjet Printer, PLoS ONE, Jul. 25, 2007).

Xu et al. discloses printing of *E. coli* directly onto agar-coated substrates using commercial ink-jet printers. (Xu et al. Construction of high-density bacterial colony arrays and patterns by the ink-jet method, Biotechnol Bioeng., Jan. 5, 2004.

Thus, there is a need for an edible product, capable of dosing a desirable amount of microorganisms to a consumer and at the same time provide an improved stability of the product and improved viability of the microorganisms present in the product.

SUMMARY OF THE INVENTION

Thus, an object of the present invention relates to an edible web comprising one or more microorganism(s). Preferably such microorganisms are non-pathogenic microorganisms, such as probiotics.

Another object of the present invention relates to a method for providing an edible web comprising one or more microorganism(s), said method comprising:
 i. providing a suspension comprising one or more microorganism(s),
 ii. providing an edible web,
 iii. printing said suspension on the edible web providing the edible web comprising one or more microorganism(s).
 iv. optionally, drying the edible web comprising one or more microorganism(s).

Yet another aspect of the present invention is to provide a food product comprising a food ingredient and an edible web comprising one or more microorganism(s) according to the present invention.

Still another aspect of the present invention relates to the use of an edible web according to the invention for dosing one or more microorganism(s).

A further aspect relates to the use of an edible web according to the invention for delivering one or more microorganism(s) to a consumer.

Yet an aspect relates to the use of an edible web for the attachment of one or more microorganism(s) to the surface of a food product such as wafers, crisps, cereals, chewing gum, pastilles, tablets or drops.

Another aspect relates to the use of an edible web for the attachment of one or more microorganism(s) onto surface of a food accessory such as straws, spoons, forks, glasses, mouthpieces of flasks, nipples of baby bottles or containers.

A further aspect relates to the use of an edible web for the attachment of one or more microorganism(s) to the surface of a baby pacifier.

Yet an aspect relates to a food accessory comprising an edible web according to the invention.

A further aspect relates to a baby pacifier comprising an edible web according to the invention.

Another aspect relates to an edible web according to the invention for use as a medicament. A further aspect relates to an edible web for use in preventing, treating and/or alleviating gastrointestinal disorders. An aspect also relates to an edible web for use in preventing, treating and/or alleviating allergy.

DETAILED DESCRIPTION OF THE INVENTION

The present invention relates to products, methods and uses relating to an edible web comprising one or more microorganism(s). It is within the scope of the invention that the embodiments described in respect of one aspect of the present may also apply other aspects of the present invention.

Microorganisms

The present invention relates to an edible web comprising one or more microorganism(s). In the present context the term "microorganism" is equal to and interchangeable with the term "microbe". The one or more microorganism(s)

according to the present invention may be any organism classified as a microorganism, in particular bacteria including probiotic bacteria, viruses, bacteriophages or any combination thereof. Although bacteriophages under certain circumstances may also be regarded as viruses, the term "virus" is in the present context to be understood as any kind of virus excluding bacteriophages. In one embodiment of the present invention, the one or more microorganism(s) is one or more bacteria, one or more bacteriophage, one or more virus or any combination hereof. In a preferred embodiment the one or more microorganism(s) is one or more bacteria.

Some microorganisms cause disease in the host in which they reside, and these microorganisms are known as pathogenic organisms. In the present context the term "pathogenic organism(s)" is interchangeable with the term "pathogen". A microorganism that does not cause disease in the host in which it resides is thus known as a "non-pathogenic organism". Preferably, the host may be a human or an animal. Although the one or more microorganism(s) according to the present invention may be any microorganism, both pathogenic and/or non-pathogenic, the microorganisms according to the invention are in a preferred embodiment a non-pathogenic microorganism.

As mentioned the edible web may comprises one or more microorganism, such as two or more microorganisms, e.g. three or more microorganisms such as four or more microorganisms.

In an embodiment of the present invention the edible web may comprise two or more different microorganisms. In this case the edible web of the present invention comprises two or more microorganisms belonging to the same class of microorganisms, such as at least two or more different bacteria or two or more different viruses or two or more bacteriophages.

In another embodiment of the present invention, the edible web comprises two or more different microorganisms belong to different classes of microorganisms, such as at one or more bacteria and one or more virus, or at one or more bacteria and one or more bacteriophage, or one or more virus and one or more bacteriophage.

In yet an embodiment of the present invention the edible web comprises three or more different microorganisms belong to different classes of microorganisms or such as one or more bacteria and one or more bacteriophage and one or more virus.

After being applied to the edible web of the present invention, the at least two or more different microorganisms are in an embodiment present in equal concentrations. However, in another embodiment of the present invention, the at least two microorganisms are present in different concentrations after being applied to the edible web. When at least three or more different microorganisms are applied to the edible web, at least two of the different microorganisms may be present in equal concentrations, while the remainder of the different microorganisms may be present in different concentration(s).

In an embodiment of the present invention the edible web may comprise one or more virus. In particular viruses that may confer a health benefit to the consumer, such as viruses that are able to activate the immune system without causing diseases, e.g. inactivated or dead viruses acting as a vaccine, are suitable viruses of the present invention. Non-limiting examples of such viruses are viruses belonging to the groups Reoviruses (Rotavirus) and/or Picornaviruses (Polio).

In another embodiment of the present invention the edible web may comprise one or more bacteriophages. Suitable bacteriophages for applying to the edible web of the present invention include bacteriophages that are directed against *Escherichia coli*, such as λ phages, T2 phages, T4 phages, T7 phages, T12 phages, R17 phages, M13 phages, MS2 phages, G4 phages, P1 phages, *Enterobacteria* phages P2, P4 phages, Phi X 174 phages, N4 phages, φ6 phages, φ29 phages and 186 phages.

However, also phages directed against other Gram-negative pathogens are suitable for applying to the web of the present invention, such as phages directed against *Salmonella, Shigella*, and other *Enterobacteriaceae, Pseudomonas, Moraxella, Helicobacter, Stenotrophomonas, Bdellovibrio*, acetic acid bacteria, *Legionella* cyanobacteria, spirochaetes, green sulfur and green non-sulfur bacteria, *Neisseria gonorrhoeae, Neisseria meningitidis, Moraxella catarrhalis, Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis* and *Salmonella typhi*.

Bacteriophages for applying to the edible web of the present invention may also include bacteriophages directed against any Gram-positive bacteria, such as bacteria belonging to the generas of *Staphylococcus, Streptococcus, Listeria, Corynebacterium, Bacillus* and *Clostridium*. Examples of such bacteriophages include, but are not limited to, SPO1-like phages, T4 phages of the gram-positive field and mycobacteriophages.

In a preferred embodiment of the present invention, the edible web comprises one or more probiotic bacteria. In the present context the terms "probiotic bacterium" or "probiotic bacteria" are interchangeable with the terms "probiotic microorganism(s)" or "probiotic(s)". Probiotics are live microorganisms that provide a health benefit to the host.

Hence, in one embodiment of the present invention the edible web comprises one or more probiotic bacteria, wherein the one or more probiotic bacteria is selected from the group consisting of *Bifidobacterium, Enterococcus, Lactobacillus* and *Streptococcus*.

In another embodiment of the present invention the edible web comprises one or more probiotic bacteria wherein the probiotic bacteria is selected from the group consisting of *Bifidobacterium bifidum, Bifidobacterium infantis, Bifidobacterium longum, Bifidobacterium breve subspecies breve, Bifidobacterium licheniformis, Bifidobacterium subtilus, Enterococcus faecium, Lactobacillus acidophilus, Lactobacillus brevis, Lactobacillus bulgaricus, Lactobacillus casei, Lactobacillus GG, Lactobacillus plantarum, Lactobacillus rhamnosus, Lactobacillus salivarius, Lactobacillus fermentum, Lactobacillus caucasicus, Lactobacillus helveticus, Lactobacillus lactis, Lactobacillus plantarum, Lactobacillus reuteri, Lactobacillus sporogenes, Streptococcus thermophilus, Streptococcus cremoris, Streptococcus faecium*, and *Streptococcus infantis*.

In a preferred embodiment of the present invention the edible web comprises *Lactobacillus acidophilus* and/or *Lactobacillus rhamnosus*.

As described herein above it is within the scope of the present invention, that the edible web comprises two or more different microorganisms. The two or more different microorganisms may in certain embodiments of the present invention be combinations of different probiotic microorganisms. Such combinations of probiotic microorganisms may be suitable for treating and/or alleviating different kinds of disorders/conditions. As an example, the combination of *Lactobacillus rhamnosus, Lactobacillus acidophilus, Lactobacillus lactis, Streptococcus thermophilus* and *Lactobacillus bulgaricus* is known to be suitable for treating/alleviating gastrointestinal disorders, while the combination of *Lactobacillus casei, Lactobacillus rhamnosus, Lactobacillus acidophilus*, and *Bifidobacterium longum* is known to be suitable for treating/alleviating food allergy conditions.

Hence in an embodiment of the present invention the edible web comprise a combination of *Lactobacillus rhamnosus, Lactobacillus acidophilus, Lactobacillus lactis, Streptococcus thermophilus* and *Lactobacillus bulgaricus*.

In another embodiment of the present invention the edible web comprise a combination of *Lactobacillus casei, Lactobacillus rhamnosus, Lactobacillus acidophilus*, and *Bifidobacterium longum*.

It is an object of the present invention to provide an edible web comprising one or more microorganisms, wherein the microorganisms have a high degree of viability, so as to provide an edible web with good storage properties and with compromising the degree of viability or at least reducing the compromise of the degree of viability. In the present context the term "viability" means the ability of a microorganism to survive and/or maintain itself and/or regain or recover its potentialities, and/or grow and/or multiply. Hence, the present invention also relates to an edible web comprising one or more microorganisms, wherein the degree of viability of the microorganism(s) after at least one week of shelf life is at least 10% relative to the total number of microorganism(s) applied to the web, such as at least 20% relative to the total number of microorganism(s) applied to the web, e.g. at least 30% relative to the total number of microorganism(s) applied to the web, such as at least 40% relative to the total number of microorganism(s) applied to the web, e.g. at least 50% relative to the total number of microorganism(s) applied to the web.

In a certain embodiment of the present invention, the edible web may comprise non-replicating microorganisms (NRMs). Such microorganisms may include the before mentioned inactivated or dead viruses, but also inactivated bacteria, e.g. dead or inactivated probiotics, and/or inactivated or dead bacteriophages may be applied to the web of the present invention.

Edible Web

The present invention relates to an edible web comprising microorganisms. In the present context the term "edible" relates to anything suitable for eating and which may be digested or partly digested when passing through the gastrointestinal system of a human or an animal. In the present context the term "web" relates to a thin and flexible material having a surface capable of comprising microorganism(s). Exemplary webs are sheets, such as substrate sheets, papers, films, foils, meshes, nets, felts, tapes and adhesives.

Thus, the present invention pertain to and edible web, wherein the web comprise an edible paper, and edible foil, an edible sheet, an edible film, an edible adhesive and/or a combination thereof. Depending on the type of edible web, the invention may relate to an edible web, wherein the web comprises a polymer.

In one embodiment of the present invention the edible web may be selected from the group consisting of sugar paper, starch paper, corn-starch paper, rice paper, soybean paper, gold paper, silver paper, fiber based paper and fiber based foils.

Depending on the type and/or the application of the edible web, said web may be laminated. In the present context the term "laminated" means the addition of at least one further layer on the edible web.

In an embodiment of the present invention, lamination of the edible web may be done before microorganisms have been printed on the surface of the edible web. In another embodiment of the present invention, lamination of the edible web may be done after microorganisms have been printed on the surface of the edible web.

Lamination of the edible web may enhance the properties of the web, including durability, appearance, adhesion, improved properties towards wear, stress and scratch, as well as improved surface properties for printing on the surface of the edible web. By laminating the edible web, the edible web may also become more resistant to the influence of humidity; sun light; physical interaction etc. and the shelf life may be improved. Lamination may also make the edible film easier to consume.

According to the invention, the edible web may be made from foodstuffs. Exemplary foodstuffs that may be used to produce the edible web of the present invention are pancakes, biscuits, confectionary products, wafers, crisps, cereals, chewing gum, pastilles, tablets or drops.

The edible web of the present invention may be made of prebiotics. In the present context "prebiotics" are non-digestible food ingredients that are able stimulate or maintain the growth and/or activity of health-beneficial bacteria in the digestive system. Prebiotics may include both carbohydrates and non-carbohydrates, and many forms of dietary fiber may exhibit some level of prebiotic effect. However, usually prebiotics relate to indigestible oligosaccharides.

In an embodiment the edible web of the present invention further comprises one or more prebiotics, thus, prebiotics have been added to the edible web. Alternatively, the edible web consists of prebiotics, thus, the entire edible web is made of one or more prebiotics Thus the present invention pertains to an edible web comprising or containing one or more prebiotics, wherein the one or more prebiotics is an indigestible oligosaccharide, preferably selected from the group consisting of inulin, fructooligosaccharides, short-chain fructooligosaccharides, galactooligosaccharides, transgalactooligosaccharides, indigestible dextrins, xylooligosaccharides, arabinooligosaccharides, glucooligosaccharides mannooligosaccharides, and isomaltooligosaccharides.

The edible web according to the present invention may further comprise one or more additives. In the present context, additives may refer to any chemical and/or biological substance that can be added to the edible web in order to enhance the physical, chemical or sensory properties of the edible web. Thus, the present invention relates to an edible web further comprising additives, wherein said additives are flavors, taste enhancing compounds, physical properties controlling agents including surface properties controlling agents, vitamins and/or nutrients or any combination thereof Method for Providing an Edible Web Comprising Microorganisms It is an objective of the present invention to provide methods for providing an edible web comprising microorganisms. Preferably, said microorganisms are applied to the web by printing. Such methods possess several advantages. Firstly, printing directly on the edible web allows for a very high degree of control of the amount of microorganism that is applied to the web, thereby allowing for very accurate dosage-control. In particular, it is possible by printing to apply a very small amount of microorganism per area of the edible web. Secondly, two or more different microorganisms may be applied to the edible web, both in independent amounts, but at the same in different separate areas of the same edible web. Hence, in an embodiment the present invention relates to a method for providing an edible web comprising one or more microorganisms, said method comprising:

i. providing a suspension comprising one or more microorganism(s),
ii. providing an edible web,
iii. printing said suspension on the edible web providing the edible web comprising one or more microorganism(s).
iv. optionally, drying the edible web comprising one or more microorganism(s).

Since different microorganisms may be printed on the same or different edible webs, it will in some instances be advantageous to dye the microorganism(s) prior to printing. Not only will dyeing of the microorganisms allow for visual confirmation that the microorganism(s) have been applied to the edible web in the right amounts, it also allows to differentiate different edible webs, or different areas of the same edible web, if the different microorganisms are dyed with different dyes prior to printing on the edible web. Furthermore, dyeing the microorganisms also allows for the investigation of the degree of viability to ensure sufficient amounts of microorganisms on the edible web. Thus, the present invention further relates to a method for providing an edible web comprising one or more microorganisms, wherein said microorganisms are dyed prior to printing.

Many different dyes with different properties suitable for visualizing microorganisms are available, and the choice of dye depends both on the microorganism to be dyed, the type of edible web onto which the dyed microorganisms are to be printed, and on the storage conditions and applications of the edible web comprising the dyed microorganisms.

In one embodiment of the present invention, the dye for dyeing the one or more microorganism(s) of the invention is selected from the group of artificial dyes consisting of Tartrazine E10 (FD&C Yellow No 5), Quinoline Yellow E104, Sunset Yellow FCF E110 (FD&C Yellow No 6), Carmoisine, Azorubin E122, Amaranth E123, Ponceau 4R E124, Erythrosine E127 (FD&C Red No 3), Red 2G E128, Allura Red AC E129 (FD&C Red No 40), Patent Blue E131, Indigotine, Indigocarmine E132 (FD&C Blue No 2), Brilliant Blue FCF E133 (FD&C Blue No 1), Green S E142, Brilliant Black BN E1515, Brown FK E154, Brown HT E155, Titanium dioxide E171 (Titanium dioxide) and any combination thereof.

In another embodiment of the present invention, the dye for dyeing the one or more microorganism(s) of the invention is selected from the group of natural or non-artificial dyes consisting of Turmeric, Natural carotene, Beta carotene, Lutein, Curcumin, Annatto, Paprika, Carminic acid, Carmine, Anthocyanin, Red beet, Blue anthocyanin, Copper chlorophyll, Chlorophyll, Carbon black, Caramel, and any combination thereof.

In yet another embodiment of the present invention, the dye for dyeing the one or more microorganism(s) of the invention is selected from the group of coloring foodstuff consisting of Tumeric Extract, Carrot, Carrot concentrate, Carthamus, Pumpkin concentrate, Black carrot, Elderberry, Aronia, Grape anthocyanin, Blackcurrant, Spirulina, Nettle, Spinach concentrate, Malt and any combination thereof.

It is further within the scope of the invention that any combination of artificial dyes, natural or non-artificial dyes and coloring foodstuff may be used to dye the one or more microorganism(s) of the present invention. Irrespective of the dye being used to dye the one or more microorganism(s), a food grade dye is preferred.

Printing of the suspension of microorganisms according to the method of the present invention may depend both on the type of microorganism(s) to be printed, the viscosity of the suspension, the type of edible web onto which the one or more microorganism(s) are to be applied, on the storage conditions and/or applications of the edible web comprising the printed microorganisms. Printing the one or more microorganism(s), optionally the one or more microorganisms that have been dyed as described above, may be performed using any printing technology including, but no limited to, screen printing, offset printing, thermal transfer, ink jet printing, lithographic blanket transfer printing, flexographic printing, letter press rotary relief plate printing, web printing, reel to reel printing, gravure printing or any combination thereof.

An embodiment of the present invention relates to a method for providing an edible web comprising one or more microorganisms, wherein step (iii) comprising printing of the suspension of dyed and/or not-dyed microorganisms is performed using an inkjet printer.

In a preferred embodiment the present invention relates a method for providing an edible web comprising one or more microorganisms, wherein step (iii) comprising printing of the suspension of dyed and/or not-dyed microorganisms is performed using a thermal inkjet printer or a piezoelectric inkjet printer.

It is within the scope of the present invention that the one or more microorganisms may be printed on the same edible web on the same area, or on the same edible web on different areas, or on one or more different edible webs. These one or more different edible webs may subsequently be combined.

As described elsewhere herein printing of the suspension of microorganisms according to the invention allows for application of very small amounts of microorganisms to the edible web in a very dosage-controllable manner. Hence, in one embodiment the present invention relates to a method for providing an edible web comprising one or more microorganisms, said method comprising printing of the suspension of microorganisms, wherein the printing droplet size is in the range of 5-100 picolitres. In another embodiment of the present invention, the diameter of the droplet after printing on the edible web is up to 80 micrometers, such as in the range of 5-80 micrometers.

Employing the method of the present invention may result in an edible web comprising microorganisms, wherein the microorganisms have a high degree of viability. The high degree of viability is an advantage when contemplating storage properties, and hence the present invention relate to a method for proving an edible web comprising microorganisms, wherein the degree of viability of the microorganisms after printing is in the range of 10-100% after one week of shelf life, such as in the range of 20-95% after one week of shelf life, e.g. in the range of 30-90% after one week of shelf life, such as in the range of 40-85% after one week of shelf life, e.g. in the range of 50-80% after one week of shelf life.

After printing the suspension of the one or more microorganism(s) onto the edible web according to the invention, the edible web comprising the one or more microorganism(s) may optionally be dried. Drying the edible web comprising microorganisms may be a crucial step because the drying procedure has to be performed under highly controlled conditions, so as ensure a maximum degree of viability of the microorganisms of the present invention after the drying process. Controlling both the temperature and timeframe in which the drying is performed may be important to ensure a high degree of viability of the microorganism.

In one embodiment of the present invention, the drying procedure of step (iv) may be performed for at most 8 hours, such as at most 6 hours, e.g. at most 4 hours, such as at most 2 hours, e.g. at most 1 hour, such as at most 45 minutes, e.g.

at most 30 minutes, such as at most 20 minutes, e.g. at most 15 minutes, such as at most 10 minutes, e.g. at most 5 minutes, such as at most 2 minutes, such as at most 1 minute, e.g. at most 30 seconds.

In another embodiment of the present invention, the drying procedure of step (iv) is performed for at a temperature of up to 90 degrees Celsius (° C.), such as up to 80 degrees Celsius, e.g. up to 70 degrees Celsius, such as up to 60 degrees Celsius, e.g. up to 50 degrees Celsius, such as up to 40 degrees Celsius, e.g. up to 30 degrees Celsius, such as up to 25 degrees Celsius, e.g. up to 20 degrees Celsius, such as in the range of 0-90 degrees Celsius, e.g. in the range of 5-70 degrees Celsius, such as in the range of 10-50 degrees Celsius, e.g. in the range of 15-35 degrees Celsius, such as in the range of 20-30 degrees Celsius.

Food Products

Important applications of the edible web comprising microorganisms of the present invention are in health-care and/or medical nutrition. Hence, in an embodiment the edible web comprising microorganisms of the present invention relates to a Food for Special Medical Purpose (FSMP). In the present context, a Food for Special Medical Purpose is a dietary food that belongs to one or more of the following categories as laid down in the EU Commission Directive 199/21/EC:

1. nutritionally complete foods with a standard nutrient formulation which, used in accordance with the manufacturer's instructions, may constitute the sole source of nourishment for the persons for whom they are intended;

2. nutritionally complete foods with a nutrient-adapted formulation specific for a disease, disorder or medical condition which, used in accordance with the manufacturer's instructions, may constitute the sole source of nourishment for the persons for whom they are intended. These foods may also be used as a partial replacement or as a supplement to the patient's diet;

3. nutritionally incomplete foods with a standard formulation or a nutrient-adapted formulation specific for a disease, disorder or medical condition which are not suitable to be used as the sole source of nourishment. These foods may also be used as a partial replacement or as a supplement to the patient's diet.

The present invention further relates to a food product comprising a food ingredient. A food ingredient in the present context pertains to any edible substance that provides nutrition and/or energy, usually in the form of proteins, carbohydrates and/or lipids, to the consumer, e.g. in the form of ready-to-consume food and/or formula. A food product in the present context is the combination of the food ingredient and the edible web according of the present invention.

In one embodiment, the food product of the present invention comprises a food ingredient and an edible web comprising one or more microorganism(s). It is also within the scope of the present invention that the food product may comprise two or more different food ingredients and/or two or more different edible webs comprising one or more different microorganism(s).

The food ingredient and the edible web comprising the one or more microorganisms which together form the food product of the present invention may be separate entities. However, in a certain embodiment the food product of the present invention comprises a food ingredient encompassing the edible web according to the present invention. In another embodiment of the present invention, the food product comprises a food ingredient that is totally or partly wrapped by the edible web comprising one or more microorganism(s).

In an embodiment of the present invention the food ingredient may be any ready-to-consume food and/or formula such as, but not limited to, dairy products, cereal products, ice cream, chocolate and chocolate bars, biscuits, snacks, crackers, wafters, coffees, teas, ready-to-drink products, health-care products, baby foods, infant fomulars, pet foods and performance food.

In the present context the term "performance food" relates to any kind of food developed with the purpose of enhancing performance of e.g. athletes. Such performance food may be any food with enhanced properties towards gaining muscle mass, providing elevated energy and endurance, providing enhanced wakefulness, providing enhanced stress tolerance, providing enhanced performance towards tackling nervousness, providing enhanced feeling of wellbeing, providing faster workout recovery, providing enhanced immune response, providing weight management and providing increased general strength and health.

Examples of performance food include, energy bars, energizer bars, energy drinks, energizer drinks, protein rich supplements, carbohydrate rich supplements and vitamin and/or nutrition rich supplements.

Uses

As explained herein above, printing the one or more microorganism(s) directly on the edible web provides for a more accurate dosage-control. Therefore, the present invention relates to use of an edible web comprising one or more microorganism(s) for dosing said one or more microorganism(s).

Further, the present invention also pertains to use of an edible web comprising one or more microorganism(s) for delivering one or more microorganism(s) to a consumer. The consumer may be any consumer capable of consuming the edible web comprising one or more microorganism(s), in particular a human or an animal.

Additionally, the present invention relates to the use of an edible web comprising one or more microorganism(s) for attachment to various surfaces, including the surfaces of food products or food accessories. The attachment of the edible web to these surfaces may be performed by lamination or coating of said surfaces with the edible web of the invention. Thus, the invention pertains to use of an edible web comprising one or more microorganism(s) for the attachment of one or more microorganism(s) to the surface of a food product such as wafers, crisps, cereals, chewing gum, pastilles, tablets or drops.

Further, the present invention relates to use of an edible web comprising one or more microorganism(s) for the attachment of one or more microorganism(s) to the surface of a food accessory such as straws, spoons, forks, glasses, mouthpieces of flasks, nipples of baby bottles or containers.

The present invention also relates to use of an edible web comprising one or more microorganism(s) for the attachment of one or more microorganism(s) to the surface of a baby pacifier.

Other Products

The present invention further relates a food accessory comprising an edible web comprising one or more microorganism(s). Examples of such food accessories are, but not limited to, straws, spoons, forks, glasses, mouthpieces of flasks, nipples of baby bottles or containers.

The present invention further relates a baby pacifier comprising an edible web comprising one or more microorganism(s).

The edible web comprising one or more microorganism(s) may be attached to the food accessory and/or the baby pacifier by lamination, coating or by using an adhesive. In this way the food accessory and/or the baby pacifier may be partly or completely covered by an edible web comprising one or more microorganism(s).

Medical Uses

As described above, the edible web comprising microorganisms of the present invention may relate to Food for Special Medical Purpose, and since the present invention may provide health beneficial microorganisms, the present invention also relates to an edible web comprising one or more microorganism(s) for use as a medicament.

The present invention also relates to an edible web comprising one or more microorganism(s) for use in preventing, treating and/or alleviating gastrointestinal disorders. Specifically, the present invention relates to an edible web comprising one or more microorganism(s) for use in preventing, treating and/or alleviating gastrointestinal disorders, wherein the gastrointestinal disorders is selected from the group consisting of irritable bowel syndrome, clostridial colonization, Traveler's diarrhea, diarrhea associated with rotaviras gastroenteritis, acute non-specific diarrhea, Constipation, chronic gas pain and colitis.

The present invention further relates to an edible web comprising one or more microorganism(s) for use in preventing, treating and/or alleviating allergy. Specifically, the present invention relates to an edible web comprising one or more microorganism(s) for use in preventing, treating and/or alleviating allergy, wherein the allergy is selected from the group consisting respiratory allergy, food allergies, lactose intolerance and allergic rhinitis.

It should be noted that embodiments and features described in the context of one of the aspects or embodiments of the present invention also apply to the other aspects or embodiments of the invention.

The invention claimed is:

1. A method for providing an edible web comprising probiotic bacteria, the method comprising:

providing a suspension comprising two or more different microorganisms;

providing the edible web, wherein the edible web comprises an edible material selected from the group consisting of sugar paper, starch paper, corn-starch paper, rice paper, soybean paper, gold paper, silver paper, fiber based paper, fiber based foil, and combinations thereof;

printing the suspension on the edible web; and applying the edible web to a substrate selected from the group consisting of a food accessory and a pacifier, wherein the food accessory is selected from the group consisting of straws, spoons, forks, glasses, mouthpieces of flasks, nipples of baby bottles, and containers.

2. The method according to claim 1, wherein the probiotic bacteria are dyed prior to printing.

3. The method according to claim 1, wherein the printing of the suspension is performed using an inkjet printer.

4. The method according to claim 1, comprising drying the edible web comprising the two or more different microorganisms.

5. The method according to claim 4 wherein the drying is performed at a temperature of up to 90 degrees Celsius (° C.).

6. The method according to claim 1, wherein the microorganisms comprise *Lactobacillus rhamnosus, Lactobacillus acidophilus, Lactobacillus lactis, Streptococcus thermophilus* and *Lactobacillus bulgaricus*.

7. The method according to claim 1, wherein the microorganisms comprise *Lactobacillus casei, Lactobacillus rhamnosus, Lactobacillus acidophilus*, and *Bifidobacterium longum*.

8. The method according to claim 1, wherein a printing droplet size is in the range of 5-100 picolitres.

* * * * *